US00PP19066P2

(12) United States Plant Patent
Smit

(10) Patent No.: US PP19,066 P2
(45) Date of Patent: Aug. 5, 2008

(54) ***IMPATIENS* PLANT NAMED 'SILTE PUR'**

(50) Latin Name: *Impatiens walleriana*
Varietal Denomination: Silte Pur

(75) Inventor: Erik Smit, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/786,128

(22) Filed: Apr. 11, 2007

(51) Int. Cl.
*A01H 5/00* (2006.01)

(52) U.S. Cl. ..... Plt./318.6; Plt./319

(58) Field of Classification Search ..... Plt./318.6, Plt./319

See application file for complete search history.

*Primary Examiner*—Kent L. Bell
*Assistant Examiner*—S. B. McCormick-Ewoldt
(74) *Attorney, Agent, or Firm*—Jondle & Associates, P.C.

(57) ABSTRACT

A new *Impatiens* plant particularly distinguished by double, rose-shaped, purple flowers, semi-compact, upright, outwardly spreading and mounded plant habit, free flowering, good basal branching, and moderately vigorous growth habit, is described.

1 Drawing Sheet

Figure 1:
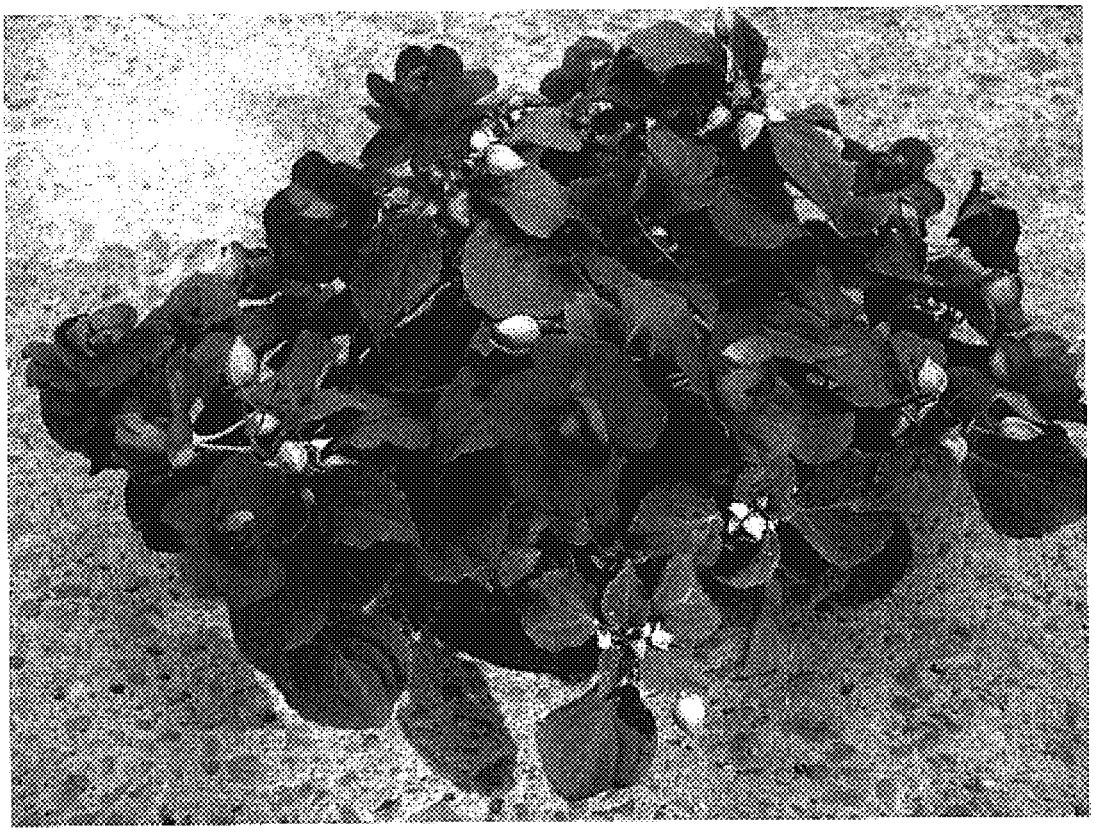

Genus and species: *Impatiens walleriana.*
Variety denomination: 'Silte Pur'.

BACKGROUND OF THE NEW PLANT

The present invention comprises a new and distinct cultivar of *Impatiens,* botanically known as *Impatiens walleriana,* and hereinafter referred to by the cultivar name 'Silte Pur'. The new cultivar originated from a hybridization made in July 2003 in Andijk, The Netherlands. The female parent was the proprietary salmon star-flowered *Impatiens* plant 'ID03-30-10' (unpatented), while the male parent was the proprietary red star-flowered *Impatiens* plant 'ID03-19-13' (unpatented). The seeds produced by the hybridization were sown in October 2003. A single plant selection was chosen for further evaluation and for asexual propagation in January 2004.

The new cultivar was created in 2003 and has been asexually reproduced repeatedly by vegetative cuttings and tissue culture in Andijk, The Netherlands and Gilroy, Calif. over a three year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar were applied for with the European Union on Nov. 13, 2006.

SUMMARY OF THE INVENTION

The following are the most outstanding and distinguishing characteristics of this new cultivar when grown under normal horticultural practices in Gilroy, Calif. and Andijk, The Netherlands.

1. Double, rose-shaped, purple flowers;
2. Semi-compact, upright, outwardly spreading and mounded plant habit; and
3. Free flowering, good basal branching and moderately vigorous growth habit.

DESCRIPTION OF PHOTOGRAPH

This new *Impatiens* plant is illustrated by the accompanying photograph which shows the overall plant habit including blooms, buds, and foliage of the plant; the colors shown are as true as can be reasonably obtained by conventional photographic procedures. The photograph is of a whole plant about 9 to 10 weeks old, grown in a greenhouse in Hillscheid, Germany during the spring. The photograph was taken in May 2006 and shows the overall plant habit including blooms, buds, and foliage.

DESCRIPTION OF THE NEW CULTIVAR

The following detailed descriptions set forth the distinctive characteristics of 'Silte Pur'. The data which defines these characteristics were collected from asexual reproductions carried out in Gilroy, Calif. in a trial setting. The plant history was taken on 22 to 24 week old plants grown in 6-inch containers in a greenhouse the fall and winter seasons. The plants had one plant growth regulator and one terminal pinch after cuttings were transplanted. Color readings were taken under natural light in the greenhouse in January. Color references are primarily to The R.H.S. Colour Chart of The Royal Horticultural Society of London (R.H.S.) (2001). Texture description data was viewed with a dissecting microscope.

DETAILED BOTANICAL DESCRIPTION OF THE NEW PLANT

Classification:
*Family.*—Balsaminaceae.
*Botanical.*—*Impatiens walleriana.*
*Common name.*—*Impatiens.*

Parentage:
*Female parent.*—'ID03-30-10' a proprietary salmon star-flowered *Impatiens* plant (unpatented).
*Male parent.*—'ID03-19-13' a proprietary red star-flowered *Impatiens* plant (unpatented).

Growth:

*Form.*—Semi-compact, upright, outwardly spreading and mounded plant habit.

*Growth and branching habit.*—Free flowering; good basal branching, moderately vigorous, pinching of the terminal apices enhances branching.

*Height* (*from soil level to top of blooms*).—16.0 cm to 20.0 cm.

*Width* (*including flower*).—40.0 cm to 45.0 cm.

*Time to produce a finished flowering plant.*—About 8 to 10 weeks for a 4-inch pot.

*Outdoor plant performance.*—Use in shade to semi-shade, use in hanging baskets, mixed containers, window boxes and mass plantings.

*Time to initiate and develop roots.*—Approximately 16 to 21 days at 22° C.

*Root description.*—Fibrous, fleshy, white.

Branches:

*Stem.*—Color: RHS 146D with RHS 183D anthocyanin. Length: 20.0 cm to 22.0 cm. Diameter: 0.5 cm. Internode length: 1.0 cm to 2.0 cm. Texture: Glabrous.

*Peduncle.*—Color: RHS 144C. Length: About 3.0 cm to 3.6 cm. Diameter: 0.15 cm. Texture: Glabrous.

Leaves:

*Arrangement.*—Mostly alternate in whorls.

*Size.*—Length: 5.5 cm to 6.5 cm. Width: 3.4 cm to 3.6 cm.

*Shape.*—Ovate.

*Apex.*—Cuspidate.

*Base.*—Attenuate.

*Margin.*—Crenate, with cillation.

*Color* (*immature leaves*).—Upper surface: Slightly lighter than RHS 147A. Lower surface: RHS 148B with RHS 176B blotches of anthocyanin.

*Color* (*mature leaves*).—Upper surface: A little darker than RHS 147A. Lower surface: RHS 148B with RHS 176B blotches of anthocyanin.

*Texture.*—Glabrous.

*Venation color.*—RHS 145C.

*Petioles.*—Length: 0.4 cm to 1.0 cm. Diameter: 0.25 cm. Color: RHS 145C. Texture: glabrous.

Flower buds:

*Shape.*—Ovate.

*Size.*—Length: 1.1 cm to 1.2 cm. Diameter: 0.8 cm to 0.9 cm.

*Color at tight bud.*—RHS N57C.

Inflorescence:

*Blooming habit.*—Continuous and freely, all through the year, depending on light levels.

*Type.*—Raceme in leaf axis.

*Number of flowers per inflorescence.*—4 to 6, including buds.

*Lastingness of the individual blooms.*—About 5 to 7 days depending on environmental conditions.

*Fragrance.*—None.

Flowers:

*Form and shape of corolla.*—Double-type, rose-shaped bud opening to form a full round flower.

*Corolla size.*—Width: 4.0 cm to 4.5 cm. Depth: 2.0 cm to 2.3 cm.

*Number of petals per flower.*—20 to 25.

Petals:

*Shape.*—Obovate.

*Apex.*—Retuse.

*Base.*—Attenuate.

*Margin.*—Entire.

*Petal size.*—Length: 1.7 cm to 2.3 cm. Width: 1.5 cm to 1.8 cm.

*Color.*—Immature petals: Upper surface: Closest to RHS 61A but a little lighter. Lower surface: Between RHS 67A and RHS 67B. Mature petals: Upper surface: Closest to RHS 61A but a little lighter. Lower surface: Between RHS 67A and RHS 67B.

*Texture.*—Papillose.

Sepals:

*Quantity.*—5; 2 large sepals, 1 modified sepal with a spur and 2 small sepals.

*Texture.*—Glabrous.

*Large sepals.*—Color: Closest to RHS 155C; RHS 145A keel. Length: 1.4 cm to 1.6 cm. Width: 1.2 cm to 1.4 cm. Shape: Ovate. Apex: Cuspidate. Base: Fused. Margin: Entire. Spur: Color: RHS 161D; RHS 173A apex. Length: 3.8 cm to 4.0 cm. Diameter: 0.1 cm at the widest point.

*Small sepals.*—Color: RHS 145A. Length: 0.2 cm to 0.3 cm. Width: 0.1 cm. Shape: Ovate. Apex: Acute. Margin: Entire. Base: Fused.

Reproductive organs: Usually not developed and observed.

Fruit and seed set: No seed set observed.

Disease and insect resistance: No particular resistance or susceptibility has been observed.

COMPARISON WITH PARENTAL AND COMMERCIAL CULTIVARS

'Silte Pur' differs from the female parent 'ID03-30-10' in that 'Silte Pur' has a double, purple flower, while 'ID03-30-10' has a single, salmon flower. Additionally, 'Silte Pur' is more compact with shorter internodes and more vigor than 'ID03-30-10'.

'Silte Pur' differs from the male parent 'ID03-19-13' in that 'Silte Pur' has a double, purple flower, while 'ID03-19-13' has a single red star-flower. Additionally, 'Silte Pur' has darker leaves and shorter internodes than 'ID03-19-13'.

'Silte Pur' differs from the commercial cultivar 'Balolepurp' (U.S. Plant Pat. No. 16,500) in that 'Silte Pur' has darker stems with larger and darker green leaves than 'Balolepurp'. 'Silte Pur' has lighter petioles and longer peduncles than 'Balolepurp'. Additionally, 'Silte Pur' has a more red-purple flower color with larger flowers and fewer petals than 'Balolepurp'.

I claim:

1. A new and distinct cultivar of *Impatiens* plant as shown and described herein.

* * * * *